US012721544B1

(12) United States Patent
Tashayyod et al.

(10) Patent No.: US 12,721,544 B1
(45) Date of Patent: Sep. 1, 2026

(54) METHOD, SYSTEM AND APPARATUS FOR ULTRA-HIGH-RESOLUTION TOTAL BODY PHOTOGRAPHY

(71) Applicant: LUMO IMAGING LLC, Potomac, MD (US)

(72) Inventors: Davood Tashayyod, Potomac, MD (US); Wei-Lun Huang, Taipei (TW)

(73) Assignee: Lumo Imaging LLC, Potomac, MD (US)

( * ) Notice: Subject to any disclaimer, the term of this patent is extended or adjusted under 35 U.S.C. 154(b) by 0 days.

(21) Appl. No.: 19/172,648

(22) Filed: Apr. 8, 2025

Related U.S. Application Data

(60) Provisional application No. 63/631,051, filed on Apr. 8, 2024.

(51) Int. Cl.
*A61B 5/00* (2006.01)
*A61B 5/107* (2006.01)

(52) U.S. Cl.
CPC .......... *A61B 5/1075* (2013.01); *A61B 5/0073* (2013.01); *A61B 5/0077* (2013.01); *A61B 5/1079* (2013.01)

(58) Field of Classification Search
CPC ... A61B 5/1075; A61B 5/0073; A61B 5/0077; A61B 5/1079
See application file for complete search history.

(56) References Cited

U.S. PATENT DOCUMENTS

2016/0139039 A1* 5/2016 Ikehara .................. G03B 15/02 348/46
2021/0251516 A1* 8/2021 Pai ......................... A61B 6/545
2022/0331028 A1* 10/2022 Sternitzke ............ A61B 5/1176
2023/0015717 A1* 1/2023 Wang .................. A61B 5/0077

FOREIGN PATENT DOCUMENTS

CN 116959093 A * 10/2023 ............. G06V 40/20
CN 117138241 A * 12/2023 ........... A61N 5/0616
WO WO-2009058996 A1 * 5/2009 ........... A61B 5/0064

OTHER PUBLICATIONS

The CN-116959093—machine translation (Year: 2023).*
The CN-117138241—machine translation (Year: 2023).*

* cited by examiner

*Primary Examiner* — Alexei Bykhovski
(74) *Attorney, Agent, or Firm* — IP Consulting Group; Michael Razavi; Alfred F. Hoyte, Jr.

(57) ABSTRACT

A method and apparatus for ultra-high resolution total body photography is provided. The method uses one or more depth cameras to do an initial scan of the subject. The scan captures depth information unique to the subject that will be used by scanning software to compute the flight path and angular position of all cameras during the scan. Given a 3D mesh of the subject obtained by the depth cameras, an Expectation-Minimization (EM) algorithm is used to assign points on the mesh uniquely to cameras and then solve for a focus distance for each camera given the associated point set.

19 Claims, 8 Drawing Sheets

(a) System design (b) Scan scheme (a) System design (b) Scan scheme

METHOD, SYSTEM AND APPARATUS FOR ULTRA-HIGH-RESOLUTION TOTAL BODY PHOTOGRAPHY

FIELD OF THE INVENTION

The invention relates generally to imaging devices. More specifically, the invention relates to a method and apparatus for high resolution total body photography.

BACKGROUND OF THE INVENTION

The present invention disclosure is directed to a method and apparatus for full body imaging or total body photography (TBP). TBP systems are used to scan a person's skin to check for and monitor lesions, moles, scars, pigmentation as well as other changes, etc., which may indicate the presence of skin cancer (e.g. melanoma) or other conditions. The output of these systems is a series of photographs that attempt to capture a large percentage of the patient's body in sharp focus. These images can be used to diagnose various skin conditions by, a dermatologist or an algorithm, to determine if there are any skin conditions requiring treatment, and also assessing the effectiveness of any ongoing treatment regimen.

Known TBP systems suffer from several drawbacks. First, prior systems tend to have inadequate resolution for effective clinical decision making. The images from other systems may also be inadequate for a number of reasons. For example if the subject distance to camera distance varies a great deal, while some camera poses can be captured with enough resolution while the farther camera to body distanced images may not. In other scanners the individual image's field of view may be too large and/or the resolution of the camera can be too low. Also the other systems may not pose the cameras optimally as the contours of the human body are not accurately accounted for. Accordingly, some photographs have higher resolution than others as the camera to subject distance varies and the depth of field of the cameras is limited.

SUMMARY OF THE INVENTION

A method and apparatus for ultra-high resolution total body photography is provided. The method uses one or more depth cameras to do an initial scan of the subject. The scan captures depth information (i.e. 3D model or 3D Mesh) unique to the subject that will be used by scanning software to compute and set the best camera parameters (e.g. camera pose and camera focus distance) for each image during the scan. In one scanner embodiment that allows varying focus distances (but does not allow camera pose variances. In other words camera poses cannot be individually controlled using robotics), given a 3D mesh of the subject obtained by the depth cameras and a scanner hardware that only allows for focus variations, an Expectation-Minimization (EM) algorithm can be used to assign points on the mesh uniquely to each camera pose and then solve for a focus distance for each camera pose given the associated point set.

The depth of field of a camera is a limiting factor for the scanners that capture images with smaller field of view and/or larger sensor sizes, such as total body photography, archaeology, and other close-range photogrammetry applications. Furthermore, in multi-view capture, where the target is larger than the camera's field of view, an efficient way to optimize surface coverage captured with quality remains a challenge. In the scanner embodiment in section [004], the inventive EM and k-view algorithms can improve the relative cost of the baseline single-view methods by at least 24% and 28% respectively, corresponding to increasing the in focus surface area by roughly 1550 cm2 and 1780 cm2. The proposed system achieves an average resolution of 0.068 mm/pixel and 0.0566 mm/pixel with approximately 85% and 95% of surface area in-focus.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 6A-6C show another alternative embodiment of the apparatus of the invention.

DETAILED DESCRIPTION OF THE INVENTION

Figure 1:
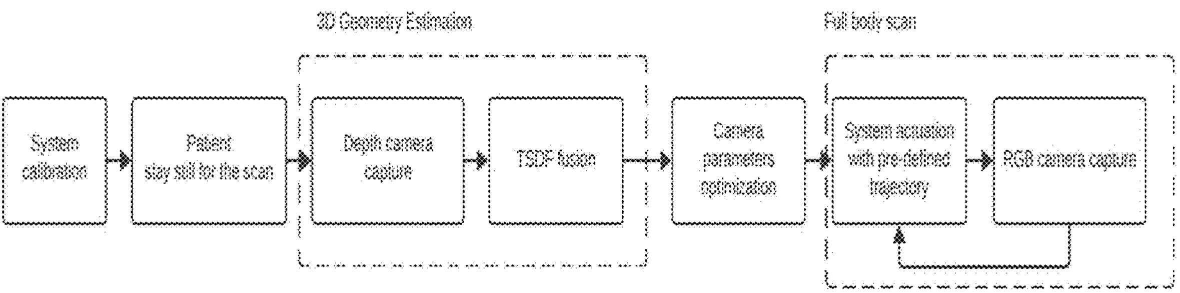
FIG. 1 is a flowchart depicting the method of the invention.

A flowchart depicting an embodiment of the software operations controlling the camera positioning and poses is shown in FIG. 1. The flowchart illustrates a sequential workflow initiated by system calibration. This calibration procedure determines the three-dimensional spatial coordinates of camera poses (position and angular orientation relative to the segment of skin captured) within a scanning apparatus and requires execution only once, provided the hardware configuration of cameras and robotic components remains unmodified. Following calibration, the subject assumes a predetermined position and maintains immobility. The computer system then activates the depth cameras, which commence acquisition of depth maps. This acquisition phase may incorporate systematic movement of the scanning apparatus concurrent with image capture. Upon collection of depth images and corresponding camera pose data, the computer executes Truncated Signed Distance Function (TSDF) fusion algorithms to consolidate the depth maps and generate a comprehensive three-dimensional point cloud representation (mesh) of the subject. Subsequently, the computer processes the point cloud data in conjunction with camera pose information to optimize focus distances for each camera.

Figure 2:
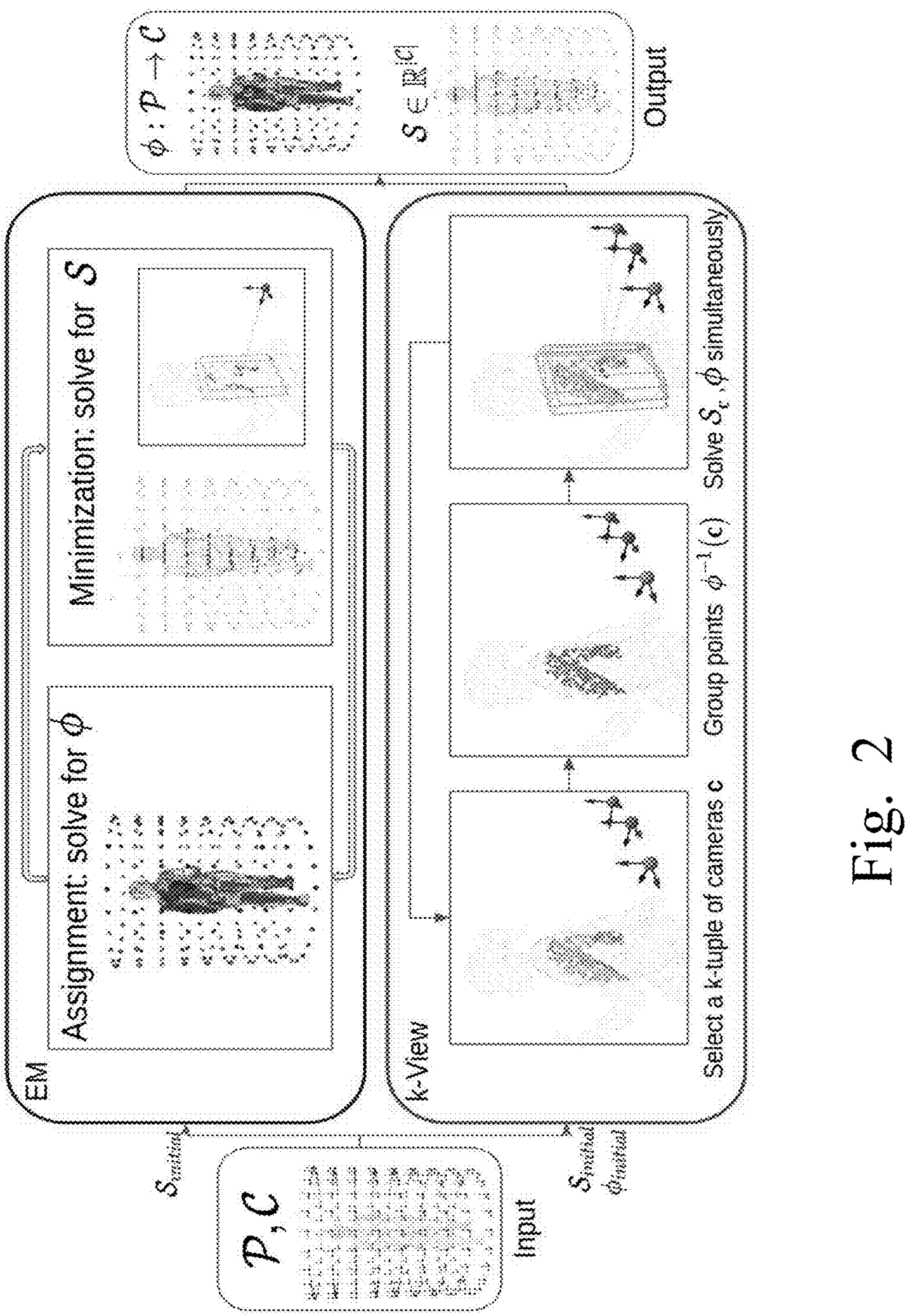
FIG. 2 is an illustration of the EM and the k-view method of solving for camera poses and focal distance.
Figure 3:
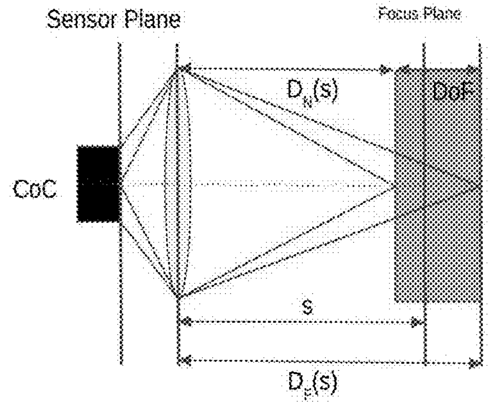
FIG. 3 is a diagrammatic illustration of the apparatus of the invention detailing the variables used for the EM and k-view method.
Figure 3:
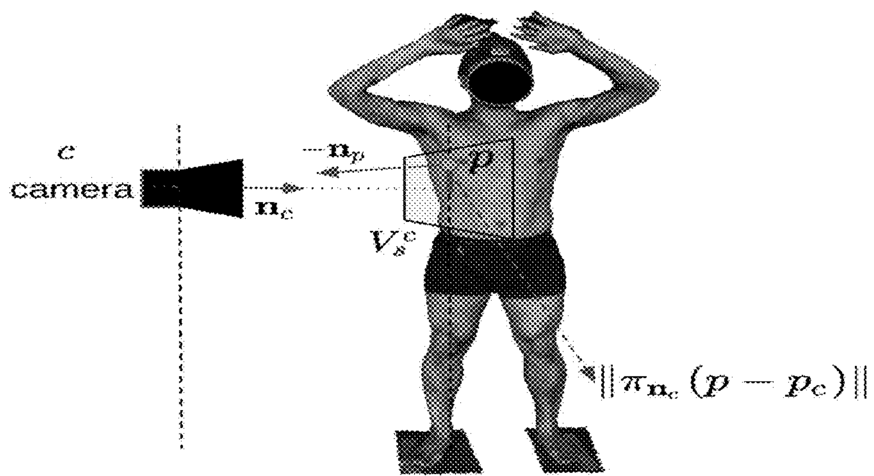

Referring now to FIGS. 2 and 3 an illustration diagramming the EM and the k-view method of solving for camera poses and focal distance is shown. FIG. 4A shows an embodiment of the apparatus which employs the method and will be discussed in more detail later. The input is the point cloud of the target P and cameras C. The output is the point assignment function $\phi$: $P \rightarrow C$ and the focus distances $S \in \mathbb{R}^{|C|}$. FIG. 3 is a diagrammatic illustration of the apparatus of the invention detailing the variables used for the EM and k-view method. Given a mesh M (obtained by scanning with a depth camera) and camera poses $C \subset SE(3)$, the inventive methods solves for an assignment of focus distances $S \in R|C|$ to cameras that reduces the size of "poorly" imaged surfaces. The focus distances are calculated in three steps:

(1) assigning a per-camera cost to each point of surface,
(2) defining the cost per-point as the minimum cost over all cameras, and
(3) seeking the focus distances that minimize the integrated cost over all Points.

Focus Distance Cost

Given a camera c E C and a focus distance s E R, we define a pointwise cost function $$\kappa_s^c : M \to [0, 1].$$

The function is set to one (the maximum cost) for all surface points $p \in M$ that are invisible to camera c. Otherwise, the cost for a given point is determined by the projected area on the image plane, its deviation from the optical axis due to field curvature, and the proximity to the focal plane. Formally we define the cost as:

$$\kappa_s^c(p) = w_1 \cdot \min\left(\frac{\varepsilon_1 \langle p - p_c, \vec{n}_c \rangle^2}{\langle \vec{n}_c, \vec{n}_p \rangle}, 1\right) \text{ — projected area}$$
$$+ w_2 \cdot \min\left(\frac{\| \pi_{\vec{n}_c}(p - p_c) \|}{\varepsilon_2}, 1\right) \text{ — optical axis deviation}$$
$$+ w_3 \cdot (1 - 1(p \in V_s^c)) \text{ — proximity to focal plane}$$

In the projected area term, the projection area of a 3D patch is a function of the depth (the distance along the optical axis of the camera) and incidence (the alignment between the viewing direction and the surface normal). Note that we define the surface normals as inward-pointing. ε1 is a threshold for the projected area so that the projected area term approaches zero for an infinite projected area and goes to 1 for a zero projected area. In the optical axis deviation term, the deviation is defined by the distance between the projection of the point p and the image center on the image plane. ε2 is a threshold so that the optical axis deviation term equals zero for a point projected onto the image center and approaches 1 for infinite deviation. We scale and clamp individual terms to the range [0,1] and apply equal weights, wi=⅓, to all terms. A visualization of the cost determining factors is shown in FIG. 3. Visualization for the cost-determining factors and the principle of the depth of field. In (a), the orange frustum ($Vc\ s \subset R3$) is clipped at the near and far depth of field (DoF) limits. The red line represents the deviation from the optical axis. In (b), CoC is the circle of confusion, s is the focus distance, and DN(s) and DF(s) are the near and far depth of field limits.

Total Cost

We define the total focus distance cost, K: $R^{|C|} \to R^{\geq 0}$ by integrating over all points, the minimal pointwise cost over all cameras:

$$K(S) = \int_M \kappa_S(p)dp \quad w/\kappa_S(p) = \kappa_{S_c}^c(p) \tag{2}$$

The solution is then the set of focus distances minimizing the cost:

$$S = \left(\mathcal{K}(\tilde{S}) = \int_M \kappa_{\tilde{S}}(p)dp\right) \tag{3}$$

Noting that the optimization in Eq. (3) can be expressed as a simultaneous optimization over assignments of surface positions to cameras, ϕ: M→C, and focus distances produces the standard EM problem:

$$(\phi, S) = \left(K(\tilde{\phi}, \tilde{S}) = \int_M \kappa_{\tilde{S}_{\tilde{\phi}(p)}}^{\tilde{\phi}(p)}(p)dp\right) \tag{4}$$

(The equivalence follows from the fact that any set of focus distances implicitly defines an assignment of points to cameras, with a point assigned to the camera minimizing the pointwise cost.) In practice, we approximate the solution using Monte Carlo integration. Concretely, letting $P \subset M$ be a discrete point-set, we set:

$$(\phi, S) = \text{argmin}_{(\tilde{\phi}, \tilde{S})} \sum_{p \in P} \kappa_{\tilde{S}_{\tilde{\phi}(p)}}^{\tilde{\phi}(p)}(p) \tag{5}$$

We use the EM approach for computing the assignment ϕ and focus distances S by first initializing the focus distances and then alternately fixing the focus distances and solving for the assignments, and fixing the assignments and solving for the focus distances.

Assignment Step

In the assignment step, we solve for the function ϕ: P→C given estimated focus distances S. This is done in the standard "greedy" fashion, assigning a point to the camera minimizing the cost for that point:

$$\phi(p) = \kappa_{S_c}^c(p) \tag{6}$$

Minimization Step

In the minimization step, we would like to solve for focus distances $S \in R|C|$ given the estimated assignment ϕ: P→C. As the assignments are fixed, this can be done independently for each camera, with the focus distance being the value minimizing the contribution from the assigned points.

$$S_c = \sum_{p \in \phi^{-1}(c)} \kappa_s^c(p) \tag{7}$$

Naively, we discretize the set of possible focus distances into N bins (from the closest to the furthest depth in $\phi^{-1}(c)$ w.r.t. camera c) and then find the minimizing focus distance.

k-View Optimization

Because the minimization step separately considers individual cameras, the EM algorithm may get trapped in a local minima. To mitigate this, we use an approach that jointly optimizes the assignment and focus distances for a k-tuple of cameras. Concretely, given an initial assignment ϕ: P→C and given a k-tuple of cameras $c = \{c_1, \ldots, c_k\} \subset C$ we would like to solve the assignment problem for the subset $\phi^{-1}(c) \subset P$ Partitioning Solution Space For a given camera c, using the fact that the cost from the projected area and the optical axis deviation are independent of focus distance, this reduces Eq. (7) to:

$$S_c = \sum_{p \in \phi^{-1}(c)} 1(p \in V_s^c) \tag{8}$$

That is, the optimal focus distance Sc is the distance at which the largest subset of points assigned to camera c are in its view-frustum. Since the summation in Eq. (8) is piecewise constant in s, we can find an optimal focus distance by partitioning the range of focus distances into intervals over which the summation is constant. Then, finding the optimal focus distance reduces to finding the interval over which the number of in-frustum points is maximized. We note that the partition of the solution space applies the optimization step in EM. Finally, the optimal focus distance can be set to the mid-point of the interval with maximal count. An illustration can be found in the supplement. Similarly, for a k-tuple of cameras c, we consider the partitions defined by the cameras, taking their Cartesian product to obtain a partition of the k-dimensional space of focus distances associated with $$c : I_c = I_{c_1} \times \ldots \times I_{c_k} \tag{9}$$

As before, this partition has the property that the cost, restricted to $\phi^{-1}(c)$, is constant within each cell.

Using $I_c$, we perform the joint optimization as follows:

1. Traversing the cells $\iota \in I_c$, of the partition, (a) We use the mid-point of cell $\iota$ as a candidate focus distances for the k cameras, (b) We compute the optimal assignment of the points in $\phi^{-1}(c)$, given the candidate focus distances given by the midpoint of $\iota$, (c) We compute the cost given the candidate focus distances and the associated assignment.

2. We replace focus distances for the cameras in c with the ones given by the midpoint of $\iota$ with the lowest cost. We note that setting k=1, our k-view approach can be used to minimize Equation (7), without having to discretely sample the space of focus distances at N locations. This reduces the complexity from O(nN) to O(n) and gives the exact minimum. We use this approach in our implementation of the Em baseline. For k>1, the joint optimization of both the focus distances and the assignment over the k-tuple of cameras allows us to bypass some of the local minima in the optimization landscape. In practice, for one iteration in k-view, we partition the cameras into maximally independent sets of k-tuples. We then update the focus distances and assignment for each k-tuples.

Complexity Letting $n=|\phi^{-1}(c)|$ be the number of points assigned to the k-tuple of cameras c, the number of cells in $I_c$ is $O(n^k)$ and it takes O(n) time to compute the optimal assignment and cost associated to each cell. Thus, the run-time complexity of optimizing over a k-tuple is $O(n^{k+1})$.

Figure 4:
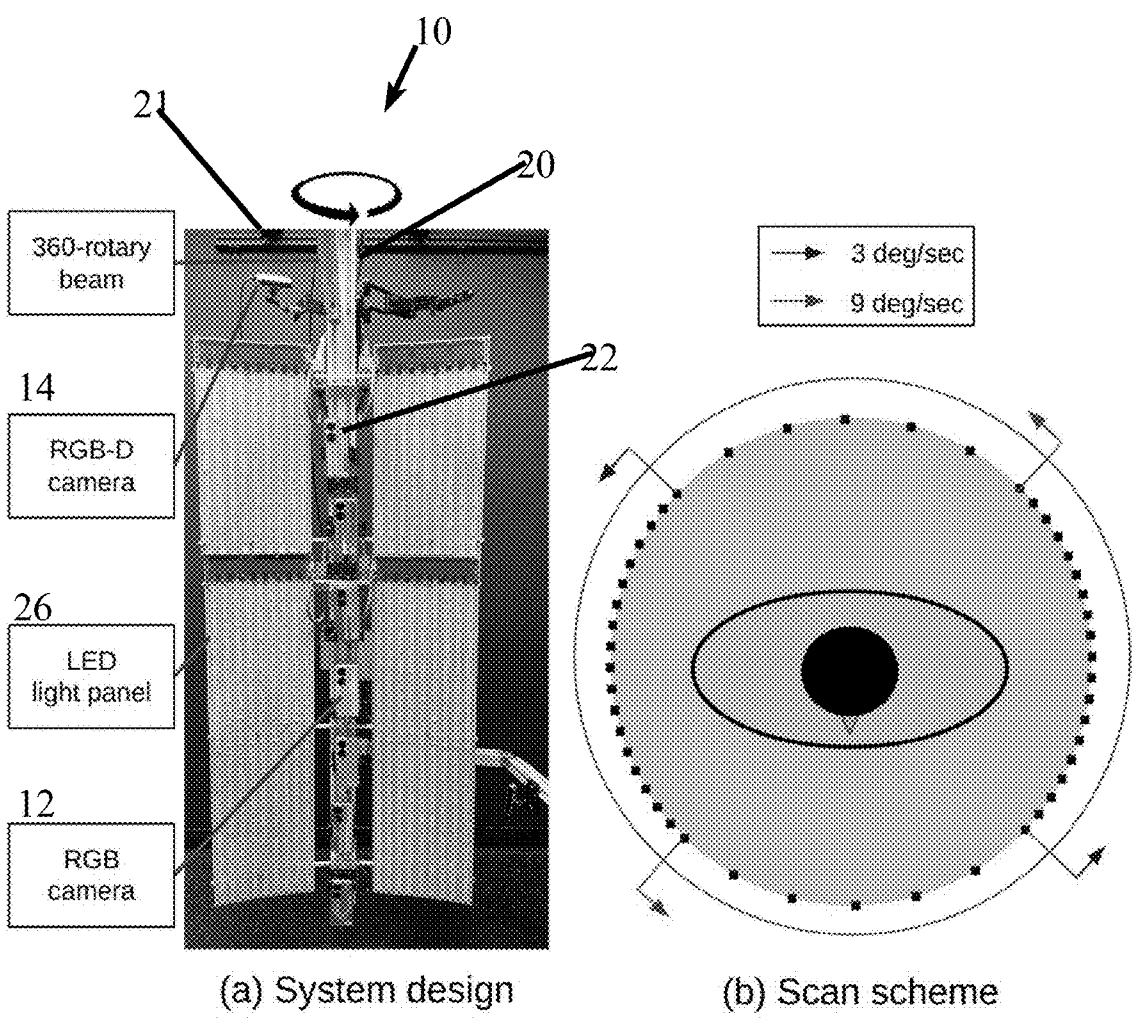
FIGS. 4A and B show the apparatus of an embodiment of the invention, with a detail of the scan pattern.

The present invention employs a novel imaging pipeline (FIG. 2) and design using the shape-aware TBP system with depth and RGB cameras on a 360-degree rotary beam (FIG. 4). Since the problem formulation requires camera poses and the 3D mesh to be given, we perform system calibration to estimate a set of poses for RGB cameras, followed by the 3D shape estimation of the subject from depth cameras. Subsequently, based on shape-aware focus, a focus distance is selected for each RGB camera pose to capture images that optimize in-focus surface coverage. Finally, the rotary beam rotates around the subject and the cameras capture images at designated poses. The shape-aware TBP system consists of three depth cam eras and seven 48-MP resolution RGB cameras on a 360 degree rotary beam, as shown in FIG. 4A. The schematic top view of the acquisition in a scan for one RGB camera is visualized in FIG. 4B. The LED light panel is used to set the ISO value of the RGB cameras to the lowest value, thereby reducing noise. Two depth cameras are installed at the side of RGB cameras, and the third depth camera is installed at the opposite side so that we can collect depth images faster to estimate the object's shape. To produce a 3D reconstruction with high-resolution textures, the RGB cameras are aligned vertically with 30%-50% overlap in the field of view for adjacent cameras. Also, each RGB camera capture images at 48 angular positions along a circular trajectory. We notice that the variation in depth is larger at the lateral regions in the designated pose, therefore, we position the cameras sparsely at the anterior and posterior regions and more densely in the lateral regions. Such an angular distribution of cameras coincides with [6] and is also beneficial for 3D reconstruction. We set two rotational speeds in a scan, 9°/sec when the system is at the front/back regions and 3°/sec for the lateral regions. The focus distance for a camera is determined for each angular position before the scan, allowing us to adjust the focus distance as the system rotates, without having to pause the acquisition.

System Calibration

Since the scanning problem assumes camera poses are given, we need to estimate a set of poses for RGB cameras denoted as $C \subset SE(3)$. To achieve this, we first estimate intrinsic camera parameters (focal length and principal point) and distortion parameters via well-established methods, denoted as $\theta$. Additionally, we design a calibration cuboid with dimensions 280×280×1800 (mm). The cuboid consists of 4 distinct ChArUco boards. The calibration cuboid is suitable for calibrating 360-degree inward-facing cameras in two folds: 1) The calibration process is well-estimated with sufficient calibration data in the subject-occupied regions, the same as the workspace of the calibration objects. 2) The ChArUco-board allows for partial visibility of the pattern in captured images and provides a unique and accurate 2D-3D correspondence.

We first detect the checkerboard corners of the ChArUco boards as keypoints in the images. We create a list of image pairs. In each image pair, we then specify the keypoint correspondences when the two images share common keypoints in the views. We perform calibration using incremental Structure from Motion (SfM). To adjust the scale of the SfM reconstruction, we estimate a similarity transformation to bring the calibration results into the real scale. To achieve this, we rely on one of the ChArUco board patterns, with a known structure and the physical size of the grids. Let $P_c$ be the target points defined in the ChArUco board coordinate and $P_{sfm}$ be its correspondence defined in an arbitrary coordinate system from the SfM. We would like to find the transformation matrix H composed of a uniform scale s, a rotation matrix $R \in SO(3)$, and a translation vector $\vec{t} \in R^3$:

$$H(s, R, \vec{t}) = \sum_i^N \left\| P_c^i - H(s, R, \vec{t}) P_{SfM}^i \right\|^2, \tag{10}$$

where N is the number of keypoints on the ChArUco board.

Since the problem formulation assumes the 3D mesh to be given, we need to estimate the 3D shape of the subject before a scan. It should be noted that for non-static objects, e.g. human subjects, the run-time for the 3D shape estimation is a limiting factor. There is a higher chance of changes in body pose and dynamic wobbling with longer running-times, leading to a divergence of the estimated shape from the real shape over the course of the scan. Two alternative methods for the 3D shape estimation of the subjects are used.

1) Template-based mesh estimation: We capture single-shot depth images from the 3 depth cameras, followed by processing with background removal, a noise filter, cropping within a pre-designed volume, computing the largest connected components, and stitching. However, the point cloud is incomplete and prevents us from determining appropriate focus distances. Several approaches have been proposed to register an SMPL model to a partial point cloud. A learned neural field dedicated to different parts of the shape is used to predict vertex displacement of the SMPL model. The parameters of the neural field are then refined using Iterative Closest Point through backpropagation. Then, the updated neural field is utilized to register the SMPL model to the input point cloud. Finally, the registration output by the network is further refined by an optimization using Chamfer distance.

2) Truncated Signed Distance Function reconstruction: Alternatively, we acquire multiple depth images with each of the 3 depth cameras. Then we compute the truncated signed distance function (TSDF) from the depth images and their poses and optimize the signed distance function. However, the collected depth images are usually noisy. To reject outliers and reduce noise, a truncation function is applied to the output value of the signed distance function. Finally, for a sequence of inputs, per-point signed distances can be estimated using the weighted average from all the frames, where the weight depends on view angles and distances. We then apply the Ball Pivoting algorithm to reconstruct a mesh given the TSDF-based point cloud.

As explained in detail above, shape-aware scanning is a two-step process for computing camera poses and focus distances of the cameras during a total body photography scan. The first step involves an estimation of the 3D geometry (in the representation of polygon mesh or point-cloud) of the subject. The second step involves an optimization method for setting camera parameters to maximize the percentage of the skin surface that meets the sharpness and high system resolution requirement to allow for effective clinical evaluation of the photographs. The system resolution is measured by the number of pixels per mm.

Three embodiments of optimization methodologies are discussed with reference to specific embodiments of the apparatus. A fixed number of camera poses (images) of 180 in a scan is assumed. The first embodiment is to start with given camera poses and to optimize for the camera focus distance at each pose. The number of degrees of freedom is 180, one per camera pose.

The second embodiment is to start with a given camera focus distance (i.e. a fixed distance to the skin surface that a camera can be placed perpendicular to its field of view) and to optimize for camera poses. The number of degrees of freedom is 1080, six per camera pose.

The third embodiment is to optimize for camera focus distances and camera poses together. The number of degrees of freedom is 1260, seven per camera pose.

A TBP system that has shape-aware scanning capability has at least several components as discussed below.

An apparatus made up of a scan module with at least one 2D RGB camera that either rotates 360 degrees around the subject by a rotary actuator, or moves from head to toe (or toe to head) motivated by two tandem linear actuators. The rotary actuator and linear actuators use commercially available gantry hardware, the implementation of which would be apparent to one of skill in the art.

One or more depth cameras (e.g. an RGBD camera). The depth information is used to estimate the 3D geometry of the subject at each juncture during the scan as discussed above.

A scan module that houses one or more cameras and possibly robotics for the movement (posing) of individual cameras. The scan module is attached to the one or more robots for moving the camera and possibly the lights for the lighting system within 3D space during the scans. It should be noted that the cameras used for 2D image captures will be equipped with longer focal length macro lenses (for longer working distance) and will be controlled through one of the camera's ports (e.g. USB port or Ethernet Port) by one or more computers. The cameras will be initialized before the scan with image capture parameters such as ISO, White Balance (i.e. 4600 degrees Kelvin), Aperture, Shutter speed. During the flight of the cameras, the camera lenses are focused at the distance necessary for the next capture, when the scan modules arrives at the precalculated position (as determined by the elapsed time or by an encoder on the linear actuator), the camera will be set with the proper setting and will be triggered remotely. A method/software for the optimization of camera parameters such as the method discussed above. The software uses the 3D geometry information (e.g. depth maps/point cloud from depth cameras) to optimize the camera focus distances and/or camera poses.

A TBP system that has shape-aware scanning capability is shown in FIG. 4A. The system allows for scanning a standing subject, and uses the first optimization method or embodiment. The embodiment of the inventive apparatus 10 shown in FIG. 4A uses a Huawei P50 Pro and Realsense D415 as the high-resolution RGB cameras 12 and the RGB-D cameras 14, respectively. The Huawei P50 Pro has a focal length of 6 mm, an aperture of f/1.8, and a sensor size of 1/1.55 inches, equivalent to a hyperfocal distance of 2,860 mm. It should be noted that the image sharpness degrades when deviating from the focal plane. Therefore, a factor of 2 is added (i.e. 5720 mm) in the depth of field calculation for tighter control of the focus distance. The capturing configuration of the Huawei camera is set to an ISO speed of 50, shutter speed of 1/500 second, and white-balance of 3500 K. The image resolutions used for the system calibration are 8192×6144 (Huawei) and 1920×1080 (Realsense). The depth image resolution for TSDF is 1280×720. The manufactured transformation from the depth camera to the RGB camera in the Realsense D415 is used to close the transformation loop from the world frame (in calibration) to the depth camera's frame.

The apparatus 10 includes a rotating actuator or gantry 20 having a beam 21 to which the scan module is securely attached, the gantry rotating the scan module 22 about the subject 24. In addition to the cameras 12 and 14, the scan module 22 includes a lighting panel 26 which may be an array of led lights or other illumination means as would be apparent to one of skill in the art. The controller for the gantry 20 may be a Yaskawa Sigma 7 controller or equivalent. The apparatus 10, which may be contained within a booth or other structure which allows for privacy, does not include robotics for individual control of the cameras.

Figure 5:
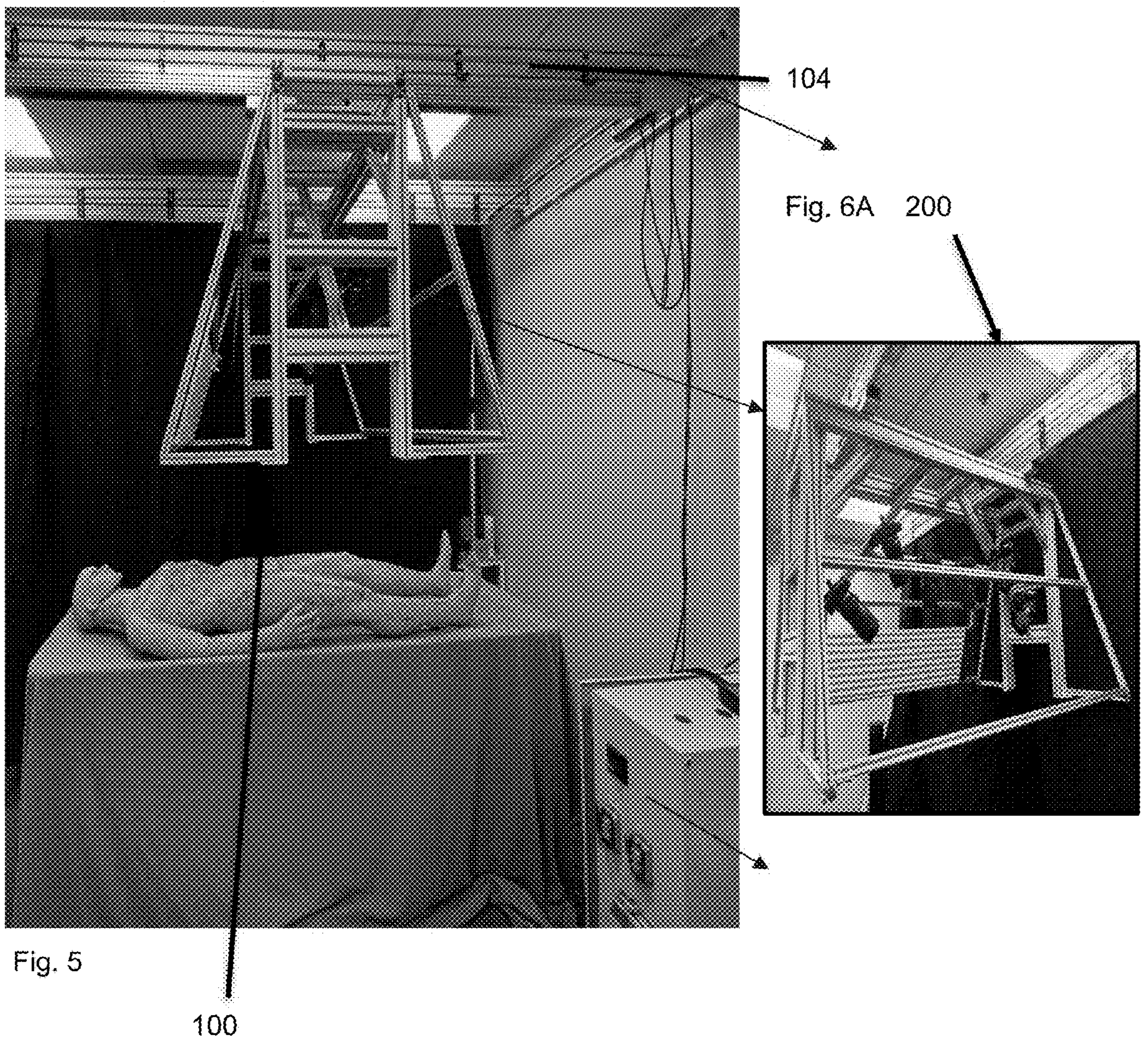
FIG. 5 shows a side view of an alternative embodiment of the apparatus of the invention.

Referring now to FIG. 5, an alternative embodiment of the TBP apparatus 100 is shown. FIG. 5 shows a recumbent embodiment without individual camera movement of the scanner hardware. It can be appreciated that a subject that is lying down is less prone to movement than a standing subject and thus the scans will give more accurate data. The recumbent variation is preferred as it gives more accurate results. This embodiment 100 is an implementation of the first embodiment of the optimization methodology. It can be seen that the apparatus 100 has an XX gantry 102 for moving the cameras 104 from head to toe (or vice versa) of the subject. The gantry controller 108 sends control signals to operate the scanner in accordance with the software of the method. An examination table 110 is used to support the subject.

Figure 6B:
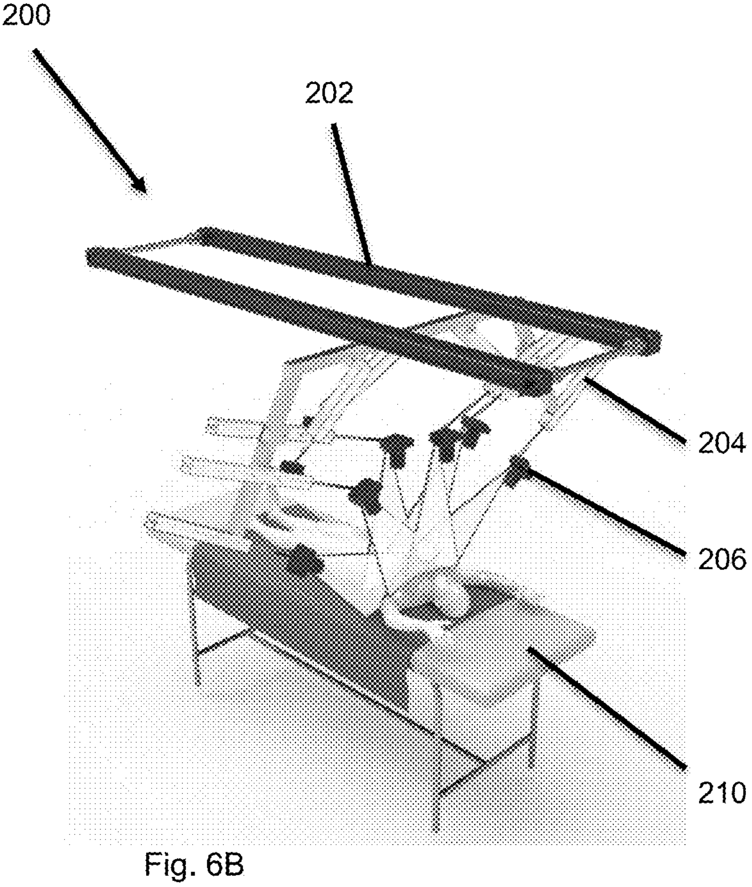
Figure 6C:
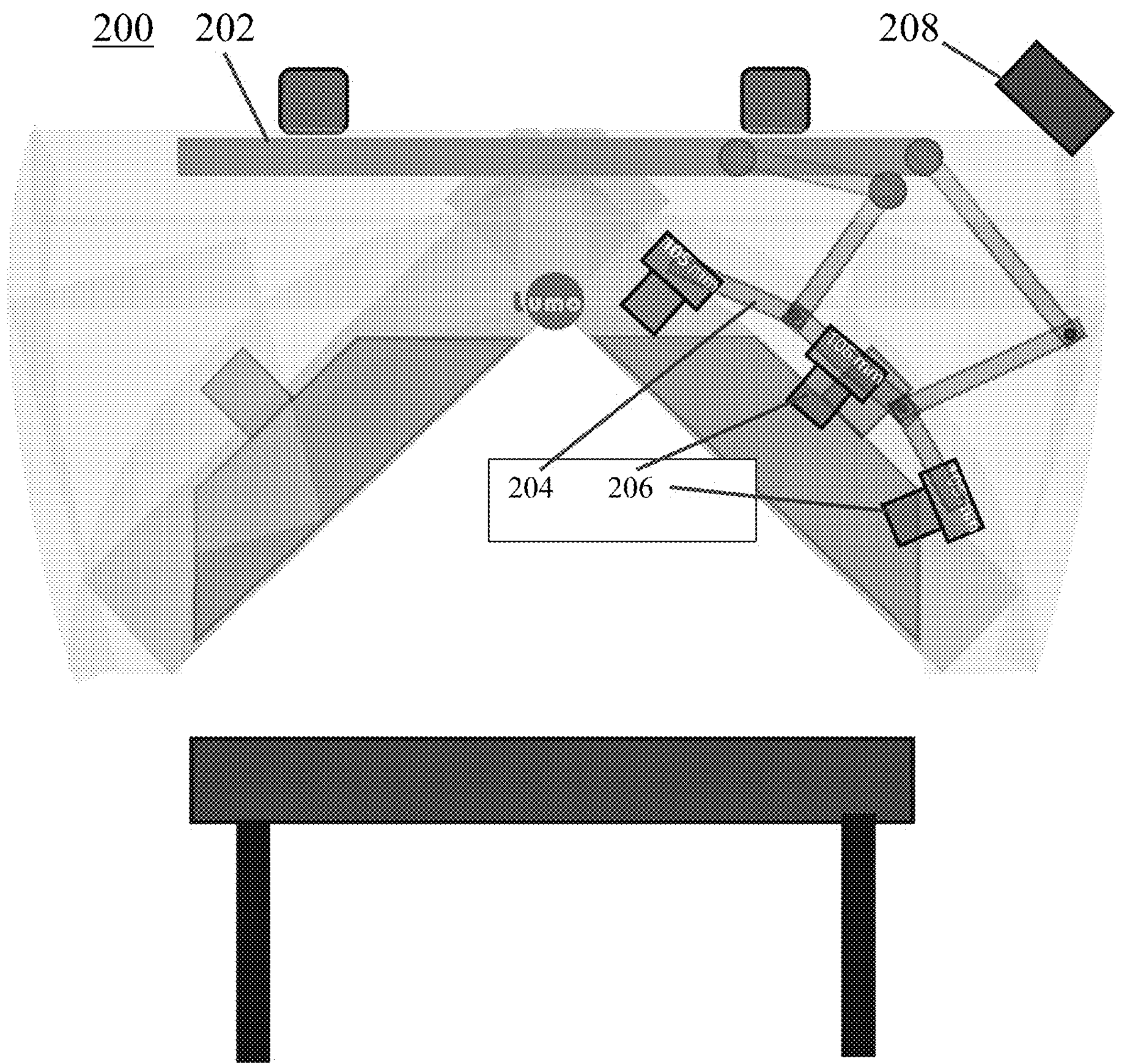

FIG. 6A-6C show a recumbent embodiment with individual camera movement of the scanner hardware. This embodiment 200 has an xx-gantry 202 supporting robotic arms 204 to which the scanning cameras 206 are attached. The robotics 204 allow for individual camera 206 movement so that the camera angle relative to the subject can be optimized. FIG. 6C shows only 3 of the 6 cameras 206 that will be mounted to the robotic arms 204 so as to clearly show the position of the robotic arms. A single depth camera 208 is attached to each side of the apparatus so that there is one depth camera for each side of the subject. The patient bed 210 is height adjustable in the well known manner.

The cameras 206 used for 2D image captures will be equipped with longer focal length macro lenses (for longer working distance) and will be controlled thru one of the camera's ports (e.g. USB port or Ethernet Port) by one or more computers. The cameras will be initialized before the scan with image capture parameters such as ISO, White Balance (i.e. 4600 degrees Kelvin), Aperture, and shutter speed. During the flight of the cameras the camera lenses are focused at the distance necessary for the next capture, when the scan modules arrives at the precalculated position (as determined by the elapsed time or by an encoder on the linear actuator), the camera will be set with the proper setting and will be triggered remotely. In one embodiment the commands for focusing and triggering of the cameras be issued to the cameras thru TTL signals for more accurate synchronization of the triggers across all camera and flashes (instead of issuing the trigger and focus command thru commination between the computer and camera thru a camera port).

With the apparatus, method and system disclosed above and given the novel approach of using the depth information captured by depth cameras, the location of camera locations will be optimized in order to capture images that are of higher magnification (closer capture distances that have been possible before) that has been possible with the previously available less sophisticated scanners. The larger number of cameras (6 in the embodiment depicted in the Figures) allows the scanner to complete the entire scan during one continuous (the scan module will never stop during the scan for minimum scan duration) and smooth motion of scan module from head to toe (though in another embodiment the same can be achieved in a back and forth motion.

Figure 7:
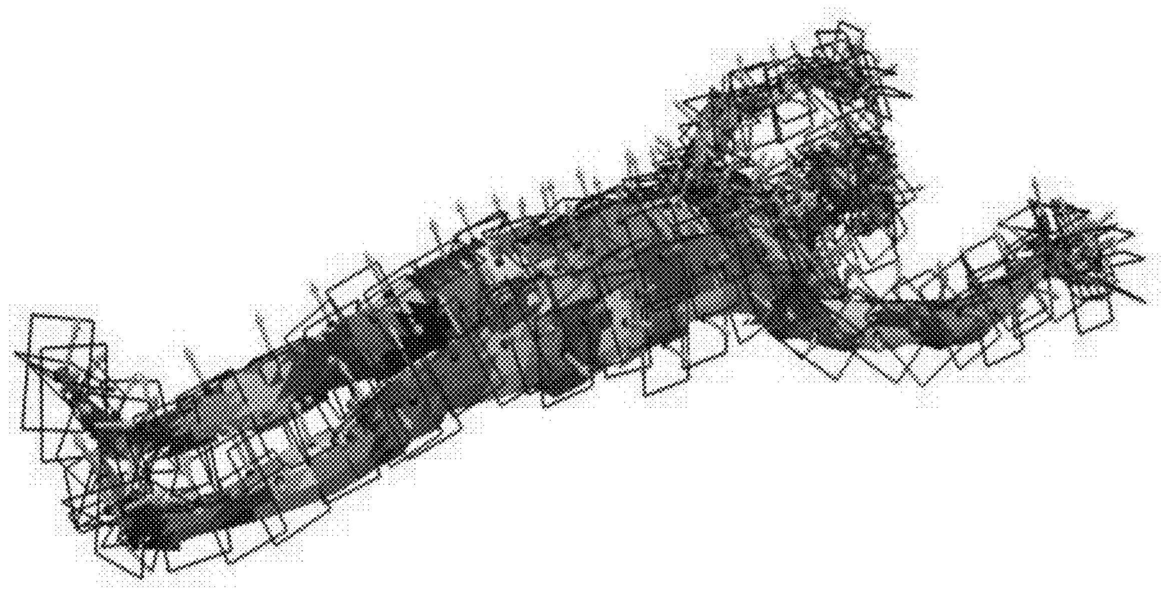
FIG. 7 shows the visualization of the optimized poses for 180 camera poses.

FIG. 7 shows the visualization of the optimized poses for 180 camera poses (for the front side of the body) perpendicular to the body surface at a distance of 55 cm. Each blue rectangle shows the field of view of a camera 206. Each arrow shows a surface normal (the opposite direction of the camera viewing direction).

This embodiment is an implementation of the second variant of the optimization. The following describes the optimization method:

Calculation of the optimal poses of 180 cameras for a 3D mesh relies on the Expectation-Minimization-algorithmic approach to optimize for maximal coverage. The algorithm alternates between two "states": camera assignment and point assignments. Initially, points are assigned to one of 180 cameras in a random clustered distribution using K-mean clustering. For each of these point clusters, the camera optimizes its position constrained by a fixed focus distance. This is done through a variety of techniques, including iterative solvers that maximize points in the field of view, sweeping window algorithms that determine the best depth of field, and density mapping to determine the most optimal viewing angle. In the second stage of point assignment, points are reassigned to a new camera which minimizes a cost function that is weighted by distance from optical axis (measure of field of view), distance for optical plane (measure of depth of field), and incidence (measure of viewing angle). These criteria in the cost function directly correlate with optimal point coverage for a camera. We alternate between these two stages of the algorithm until the cameras converge on an optimal position that minimizes the cost function—and so maximizes overall camera coverage of the points of the mesh.

There are cases that require steps of scanning the patients' body multiple times to increase the percentage of patients' body that is not occluded. Each scan adds to the percentage of captured body surface. In this scenario, each scan is responsible for capturing high-resolution image data for some body segments. For example, in a recumbent embodiment as in FIGS. 5 and 6, at least two scans are required, one for the anterior and one for the posterior of the body.

The optimization for multiple scans involves a registration from a partial scan to the entire body (in the representation of a 3D template mesh of a generic person), a partition of the skin surface of the entire body to multiple scans, and an optimization for camera parameters for each scan (this follows the optimization variants described in the optimization methodology). In one embodiment, two scans are required for the shape-aware scanning. The entire body can be divided into the anterior segment and the posterior segment. In one embodiment, four scans are required for the shape-aware scanning. The entire body can be divided into the anterior segment, right lateral segment, the posterior segment, and the left lateral segment.

Registration of Partial Scan to Template Mesh

The surface information of the partial scan can be estimated through a variety of methods such as the following two: Truncated Signed Distance Function reconstruction by fusing multiple depth maps captured by RGBD cameras and photogrammetry reconstruction using multiple RGB images from standard RGB cameras.

To register a partial scan to the template mesh, we employ a two-stage approach. First, we detect the body landmarks (e.g. body joints and facial landmarks) on both the partial scan and the 3D template mesh. For the partial scan, landmark estimation is performed on a 2D rendering of its reconstructed surface. By aligning these corresponding landmarks, we achieve an initial rough registration of the partial scan to the 3D template mesh. Second, we refine the alignment by adopting a piecewise rigid body assumption. This assumption allows us to independently align each rigid body segment of the partial scan to the corresponding segment of the 3D template mesh. Since these segment-specific alignments can be processed in parallel, we significantly reduce computational expense while maintaining accuracy.

Partition of the Skin Surface to Multiple Scans

After registering multiple partial scans to the 3D template mesh, we often encounter surface areas that have been captured in more than one scan. However, the system resolution and sharpness of these overlapping regions typically vary between different observations due to factors such as camera positioning, viewing angles, and camera focus distances.

To maximize both the average system resolution and the percentage of surface area that is captured in optimal focus, we implement a partitioning strategy for the skin surface. This process assigns each unit of surface area to a single, unique partial scan—specifically the one that provides the highest quality representation of that area.

Following this partitioning, we optimize the camera parameters (such as focus distances and camera poses) for each partial scan using an Expectation-Minimization (EM) algorithm. This optimization ensures that subsequent imaging sessions will capture each partitioned region with the best possible clarity and resolution.

Based on the reachable camera poses and the range of available focus distances, we can generate a comprehensive volume representing the accumulation of all feasible viewing frustums of the cameras. For each partial scan, using this defined volume and the targeted surface area, we can suggest an optimal body pose (from a set of candidate poses) that maximizes exposure of the targeted surface area to the imaging volume.

We claim:

1. A method of maximizing a percentage of a skin surface of a subject in sharp focus comprising the steps of:

3d information capture of a patient's body to generate a three-dimensional model of the patient's body, setting two-dimensional camera parameters, including camera poses and/or focus distances for one or more two-dimensional cameras based on said three-dimensional model to maximize (i) a resolution and (ii) a percentage of an area of the skin surface that is in sharp focus in an image acquisition, scanning and photographing with said one or more two-dimensional cameras to produce a series of images, wherein setting the two-dimensional camera parameters includes assigning portions of the three-dimensional model to respective cameras and optimizing the camera parameters based on the assigned portions, wherein the skin surface area that is in sharp focus in the image acquisition includes that the said skin surface area is captured within the depth of field of at least one image from the said image acquisition.

2. The method of claim 1, wherein said 3d information capture comprises obtaining depth information by a depth camera.

3. The method of claim 2, wherein said depth camera is an RGBD camera.

4. The method of claim 1, wherein said one or more two-dimensional cameras comprise two-dimensional cameras that are posed independently.

5. The method of claim 1, further comprising:

performing a plurality of scans of the subject; and updating the determination of the two-dimensional camera parameters for a subsequent scan based on skin surface regions previously captured in sharp focus.

6. The method of claim 5, further comprising:

registering surface information from a prior scan to a three-dimensional template mesh; and determining the two-dimensional camera parameters for the subsequent scan based on portions of the template mesh not previously captured in sharp focus.

7. The method of claim 6, wherein said registering includes aligning skeletal landmarks of the subject with corresponding landmarks of the template mesh.

8. The method of claim 6, wherein said registering assumes a piecewise rigid body.

9. The method of claim 6, wherein said surface information is obtained from at least one of:

RGBD camera data; or photogrammetry reconstruction.

10. The method of claim 5, further comprising:

selecting a pose of the subject from a set of predefined poses based on the determined camera parameters to increase coverage of skin surface not previously captured in sharp focus.

11. An apparatus for imaging all skin surfaces of a subject's body comprising:

at least one depth camera, a scan module with at least one high-resolution two-dimensional camera, robotics for posing the at least one high-resolution two-dimensional cameras, and a lighting system for illuminating the skin surfaces, and a processing unit configured to generate a three-dimensional model from the at least one depth camera and to determine two-dimensional camera parameters including camera poses and/or focus distances to maximize a percentage of the skin surface in sharp focus based on the three-dimensional model, wherein setting the two-dimensional camera parameters includes assigning portions of the three-dimensional model to respective cameras and optimizing the camera parameters based on the assigned portions, wherein the skin surface in sharp focus suggests that the said skin surface is captured within the depth of field of at least one image.

12. The apparatus of claim 1, wherein said depth camera is stationary.

13. The apparatus of claim 1, wherein said depth camera is part of the scan module.

14. The apparatus of claim 1, wherein said depth camera is an RGBD camera.

15. The apparatus of claim 1, wherein the scan module is stationary with respect to the subject's body.

16. The apparatus of claim 1, wherein a gantry is configured to move the scan module from head to toe or from toe to head of the subject's body.

17. The apparatus of claim 1, further comprising an adjustable height table, wherein the processing unit is configured to determine a recommended height for the adjustable height table based on the three-dimensional model to optimize a percentage of the skin surface that is in sharp focus.

18. The apparatus of claim 1, wherein the robotics for posing the at least one high-resolution two-dimensional camera includes pan motors.

19. The apparatus of claim 1, wherein the robotics for posing the at least one high-resolution two-dimensional camera includes pan motors, tilt motors, and actuators for moving the at least one high-resolution two-dimensional camera.

* * * * *